United States Patent [19]

Orlowski et al.

[11] Patent Number: 4,597,900

[45] Date of Patent: Jul. 1, 1986

[54] DES[2]-GLYCINE[8]-DES[22]-CALCITONIN

[75] Inventors: Ronald C. Orlowski, Frankfort; Jay K. Seyler, Bourbonnais, both of Ill.

[73] Assignee: Armour Pharmaceutical Co., Tarrytown, N.Y.

[21] Appl. No.: 525,356

[22] Filed: Aug. 22, 1983

[51] Int. Cl.[4] ............................................. C07K 7/36
[52] U.S. Cl. ................................................... 530/307
[58] Field of Search ................................ 260/112.5 T

[56] References Cited

U.S. PATENT DOCUMENTS

| | | | |
|---|---|---|---|
| 4,217,268 | 8/1980 | Hughes et al. | 260/112.5 T |
| 4,239,680 | 12/1980 | Hughes et al. | 260/112.5 T |
| 4,401,593 | 8/1983 | Orlowski et al. | 260/112.5 T |
| 4,451,395 | 5/1984 | Orlowski et al. | 260/112.5 T |

OTHER PUBLICATIONS

Noda et al., *J. Biochem.*, 79, 353–359 (1976).

*Primary Examiner*—Delbert R. Phillips
*Assistant Examiner*—F. T. Moezie

[57] ABSTRACT

New peptides are disclosed which have biological activity of the same type as known calcitonins and which have a shorter amino acid chain than natural calcitonins and are also substitution analogs of the natural calcitonins. Also resin peptides are disclosed which may be converted to peptides having such biological activity; and processes for producing said resin peptides and said calcitonin peptides.

4 Claims, No Drawings

DES²-GLYCINE⁸-DES²²-CALCITONIN

FIELD OF THE INVENTION

This invention relates to calcitonins having biological activity and to peptides which can be converted to biologically active calcitonins and to processes for preparing such peptides and calcitonins.

BACKGROUND OF THE INVENTION

All known natural calcitonin peptides contain an amino acid sequence of 32 amino acids. Salmon calcitonin, for example, has the following formula:

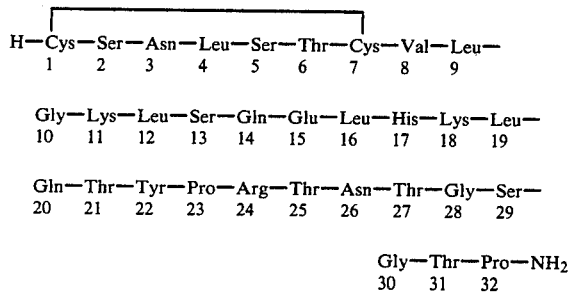

In U.S. Pat. Nos. 3,926,938, 4,062,815, 3,929,758, 4,033,940, 4,217,268 and 4,336,187 are disclosed improved syntheses of calcitonins including the salmon calcitonin referred to above.

The natural calcitonins include the salmon, eel, bovine, porcine, ovine, rat and human calcitonins. All of these have either serine or glycine at position number 2, either valine or methionine at position number 8, and either phenylalanine or tyrosine at position number 22.

SUMMARY OF THE INVENTION

We have discovered synthetic calcitonin peptides with 30 amino acids that have biological activity of the same type as the known calcitonins. A significant difference in structure is that in our new peptides the amino acid sequence does not contain either serine or glycine at position 2 or valine or methonine at position 8 or phenylalanine or tyrosine at position 22 of the known calcitonin amino acid sequence. These new peptides are termed des-X²-Gly⁸-des-Y²² calcitonin wherein X² is serine or glycine and Y²² is phenylalanine or tyrosine, using the IUPAC-IUB method of nomenclature for synthetic modifications of peptides [Biochem. Biopys. Acta, 133, 1-5 (1967)]. The new peptides have higher potency and quality when compared to known calcitonins.

DESCRIPTION OF INVENTION

In general we use a solid phase type of synthesis and start with a resin called benzhydryl amine resin (BHA resin). This resin is derived from a cross-linked polystyrene bead resin manufactured by copolymerization of styrene and divinylbenzene. Resin of this type is known and its preparation is further demonstrated by Pietta et al. [Pietta, P. S. and Marshall, G. R., Chem. Commun., 650 (1970), and Orlowski et al., J. Org. Chem., 41, 3701 (1976)]. The cross-linked polystrene BHA resin is available from chemical supply houses. We use the designation

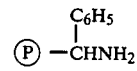

to represent the BHA resin in which Ⓟ is the polystrene portion of the resin.

RESIN PEPTIDE SYNTHESIS

In this synthesis the amino acids are added one at a time to the insoluble resin until the total peptide sequence has been built up on the resin. The functional groups of the amino acids are protected by the blocking groups. The α-amino group of the amino acids is protected by a tertiary butyloxycarbonyl group or an equivalent thereof. This α-tertiary butyloxycarbonyl group we designate as BOC. The hydroxyl functions of serine and threonine are protected by a benzyl or benzyl derivative group such as 4-methoxybenzyl, 4-methylbenzyl, 3,4-dimethylbenzyl, 4-chlorobenzyl, 2,6-dichlorobenzyl, 4-nitrobenzyl, benzhydryl or an equivalent thereof. We use the term BZ to represent the benzyl or benzyl derivative group.

The thiol function of cysteine may be protected by benzyl or benzyl derivative protective groups described above and designated BZ, or by an n-alkylthio group such as methylthio, ethylthio, n-propylthio, n-butylthio or equivalents thereof. We use the character R₂ to represent an n-alkylthio group or BZ, and the character R₁ to represent BZ when R₂ is n-alkylthio and to represent n-alkylthio when R₂ is BZ. Alternatively, R₁ may be another cysteine group and when this is the case R₂ is BZ. The guanidine function of arginine may be protected by a nitro group, a tosyl group or an equivalent thereof. We use the character T to represent either a nitro group or a tosyl group. The ε-amino function of lysine may be protected by a benzyloxycarbonyl group or a benzyloxycarbonyl derivative such as a 2-chlorobenzyloxycarbonyl, 3,4-dimethylbenzyloxycarbonyl, or equivalents thereof. We use the character V to represent benzyloxycarbonyl group or a benzyloxycarbonyl derivative group. The protective groups used on the imidazole nitrogen of histidine are the benzyloxycarbonyl group and benzyloxycarbonyl derivatives such as described above for lysine and are designated as V. The γ-carboxylic acid group of glutamic acid is protected by a benzyl or benzyl derivative group such as described for the protection hydroxyl function of serine and threonine. These protective groups are represented by the character BZ.

The formula of our new [Des-Ser²-Gly⁸-Des-Tyr²²] salmon calcitonin having activity of the same type as known salmon calcitonin may be written as follows:

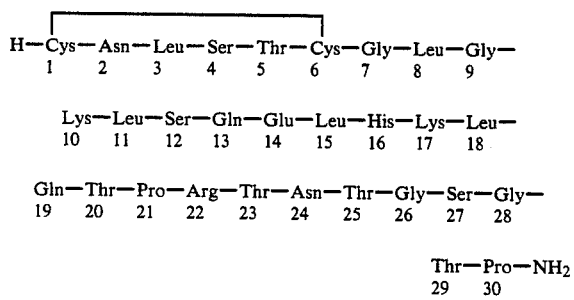

The formula of our new [Des-Ser$^2$-Gly$^8$-des-Tyr$^{22}$] eel calcitonin may be written as follows:

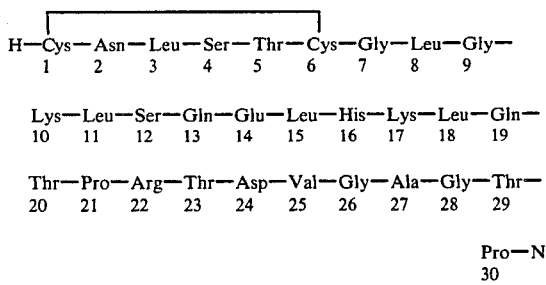

The formula of our new [Des-Gly$^2$-Gly$^8$-des-Phe$^{22}$] human calcitonin may be written as follows:

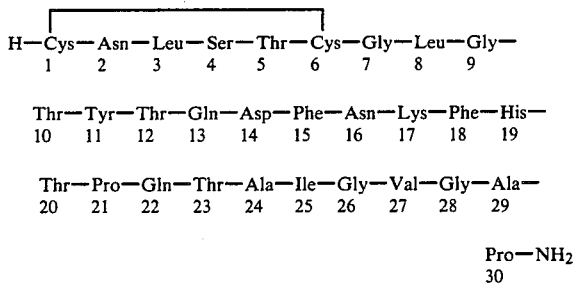

Included within the present invention are also the des-X$^2$-Gly$^8$-des-Y$^{22}$ analogs of bovine, porcine, ovine and rat calcitonin.

As may be seen from the formula given above, 30 amino acids are involved and in this formula the positions are numbered according to the accepted procedure beginning at position 1 for the CYS on one end of the chain, and ending with PRO at position 30 at the other end of the chain. For clarity of description, this same numbering system will be followed in referring to the cycles of the synthesis. The assembly of the amino acids begins with cycle 30 which involves the coupling of proline and continues with cycle 29 which involves the coupling of threonine, etc.

Preferred amino acid reactants for use in each of the 30 cycles of the synthesis of salmon calcitonin (used for exemplification only) are given in the following Table I:

TABLE I

| Cycle Number | Amino Acid Reactant |
|---|---|
| 30 | BOC—L-proline |
| 29 | BOC—O—benzyl-L-threonine |
| 28 | BOC—glycine |
| 27 | BOC—O—benzyl-L-serine |
| 26 | BOC—glycine |
| 25 | BOC—O—benzyl-L-threonine |
| 24 | BOC—L-asparagine p-nitrophenyl ester |
| 23 | BOC—O—benzyl-L-threonine |
| 22 | BOC—Ω-nitro-L-arginine or BOC—Ω-tosyl-L-arginine |
| 21 | BOC—L-proline |
| 20 | BOC—O—benzyl-L-threonine |
| 19 | BOC—L-glutamine p-nitrophenyl ester |
| 18 | BOC—L-leucine |
| 17 | BOC—ε-CBZ—L-lysine or BOC—ε-2-chlorobenzyloxycarbonyl-L-lysine |
| 16 | BOC—N(im)—CBZ—L-histidine |
| 15 | BOC—L-leucine |
| 14 | BOC—L-glutamic acid γ-benzyl ester |

TABLE I-continued

| Cycle Number | Amino Acid Reactant |
|---|---|
| 13 | BOC—L-glutamine p-nitrophenyl ester |
| 12 | BOC—O—benzyl-L-serine |
| 11 | BOC—L-leucine |
| 10 | BOC—ε-CBZ—L-lysine or BOC—ε-2-chlorobenzyloxycarbonyl-L-lysine |
| 9 | BOC—glycine |
| 8 | BOC—L-leucine |
| 7 | BOC—glycine |
| 6 | BOC—S—ethylthio-L-cysteine, BOC—S—methylthio-L-cysteine, BOC—S—propylthio-L-cysteine or BOC—S—n-butylthio-L-cysteine |
| 5 | BOC—O—benzyl-L-threonine |
| 4 | BOC—O—benzyl-L-serine |
| 3 | BOC—L-leucine |
| 2 | BOC—L-asparagine p-nitrophenyl ester |
| 1 | BOC—S—p-methoxybenzyl-L-cysteine, BOC—S—3,4-dimethylbenzyl-L-cysteine or BIS—BOC—L-cysteine |

Each of the amino acid derivatives mentioned in Table I may be purchased from supply houses.

CYCLE 30

Coupling Of Proline To BHA Resin

The reaction vessel used in all steps of the resin peptide synthesis may be a glass vessel equipped with inlet ports at the top for addition of materials and a sintered glass disk at the bottom for removal of soluble reaction mixtures and wash solvents by filtration. Filtration may be performed either by vacuum or the use of nitrogen pressure. The contents of the vessel may be agitated by shaking the entire vessel or by mechanical stirrer.

In cycle 30 the BHA resin is placed in the reaction vessel and suspended in a solvent such as methylene chloride, chloroform, dimethylformamide, benzene or equivalents thereof in proportions of about 3 to 12 ml. of solvent per gram of resin. To this is added BOC-L-proline in an amount of about 1 to 6 equivalents per free amine equivalent of the BHA resin employed. After a period of mixing of 5 to 10 minutes, a coupling reagent (CA) such as dicyclohexylcarbodiimide (DCC) may be added, or other diimide coupling agents may be used. The diimide coupling agent may be used in the amount of 0.5 to 2.0 equivalents per equivalent of BOC-L-proline used.

The BOC-L-proline may be coupled in the absence of a coupling reagent if its active ester derivative, its azide derivative, its symmetrical anhydride derivative, or a suitably chosen mixed anhydride derivative is used. Active ester derivatives that may be employed are 2-nitrophenyl ester, 4-nitrophenyl ester, pentafluorophenyl ester, N-hydroxysuccinimide ester or equivalents thereof. The active esters are used in amounts of 1 to 10 equivalents per free amine equivalent of BHA resin.

The reaction mixture consisting of the BHA resin, the solvent, the BOC-L-proline, and the coupling reagent or BOC-proline active ester is stirred or shaken mechanically until the reaction is complete as indicated by a ninhydrin test [E. Kaiser, et al., Anal. Biochem., 34, 595-8 (1970)] on a test sample. After completion of the coupling reaction, the BOC-L-proline resin may be washed with solvents such as methylene chloride, chloroform, methyl alcohol, benzene, dimethylformamide, or acetic acid. The amount of wash solvent may suitably be 5 to 20 ml. of solvent for each gram of BHA resin used initially. If it is desired to terminate the coupling reaction before completion, the washing procedure may be used and the remaining free amino groups on the BOC-L-proline resin may be blocked from further reaction by acetylation with an excess of acetylation reagents. The acetylation procedure may be performed by agitating the BOC-L-proline resin with a solution of the acetylation reagent for a period of 0.5 to 12 hours. Acetylation reagents such as N-acetylimidazole in methylene chloride solution or a mixture of acetic anhydride and triethylamine in chloroform may be used. The acetylation reagent may be used in the amount of 0.5 to 5.0 equivalents per equivalent of free amine titer of the starting BHA resin.

The coupling reaction to produce the BOC-L-proline resin may be described by the following formula:

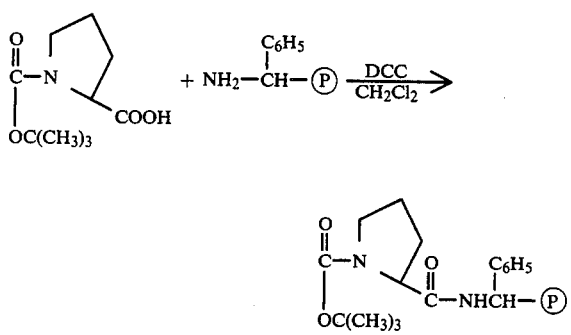

Deprotection of BOC-L-Proline Resin

The BOC-L-proline resin produced as above described may be washed with a solvent such as referred to above and deprotected by agitating it with an agent such as a mixture of trifluoroacetic acid (TFA) in a solvent such as methylene chloride, chloroform, benzene or equivalents thereof. The amount of TFA in the solvent may vary from 10 to 100% of the mixture. The amount of TFA-solvent mixture may vary from 3 to 20 ml. per gram of BHA resin used initially. The reaction time may be from about 10 minutes to 4 hours. The deprotection step is terminated by filtration to remove the TFA-solvent mixture. The residual TFA may be removed from the L-proline resin by washing with 3 to 20 ml. per gram of BHA resin of a 5 to 30% of triethylamine solution in a solvent such as methylene chloride, chloroform, benzene or equivalents thereof. Other tertiary or secondary organic amines may be used in place of the triethylamine, such as, trimethylamine, N-ethylpiperidine, diisopropylamine or equivalents thereof. The free amine titer of the L-proline resin may be determined by the Dorman titration procedure [Dorman, L. C., *Tetrahedron Letters*, 1969, 2319–21]. The deprotection reaction may be described by the following formula:

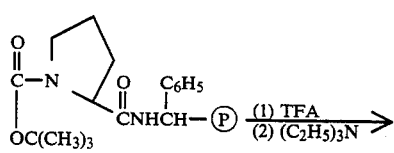

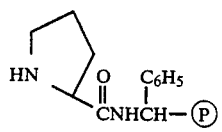

CYCLE 29

The prolyl BHA resin obtained as a result of cycle 30 may be suspended in a coupling solvent, the BOC-O-BZ-L-threonine derivative added and the mixture equilibrated in the same manner. The coupling agent, DCC, may be added, and after completion of the reaction as indicated by the isatin test [E. Kaiser, et al., *Anal. Chem. Acta*, 118, 149–51 (1980)], the reaction mixture may be removed from the BOC-O-BZ-threonylprolyl BHA resin by filtration. The peptide resin may be washed with solvents. The amounts of reactants and solvents and reaction times may be the same as described in cycle 30. The BOC group may be removed from the peptide resin by the deprotection method described in the cycle 30. The resulting O-BZ-threonylprolyl BHA resin is then ready for cycle 28. The reactions of the cycle 29 may be shown by the following formula:

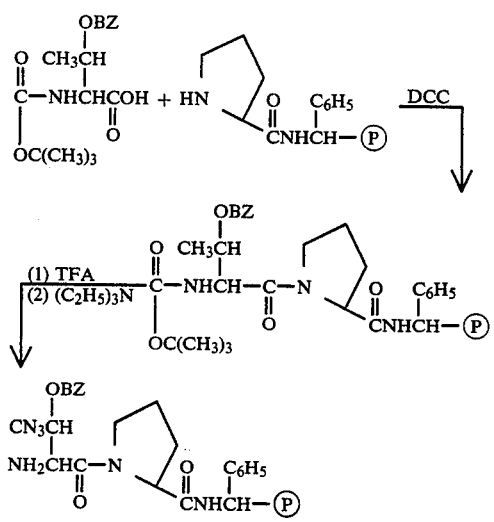

For convenience, we may write this resulting resin peptide using abbreviated nomenclature as follows:

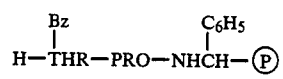

CYCLE 28

In cycle 28, the coupling reaction and also the deprotection reaction may be performed in the same manner as in cycle 29 except that BOC-glycine is used in place of BOC-O-BZ-L-threonine. The reaction through coupling and deprotection may be written:

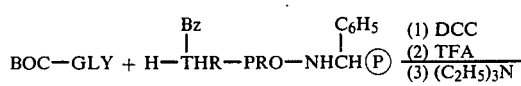

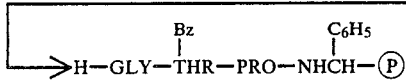

CYCLE 27

In cycle 27, the coupling and deprotection reactions may be performed in the same manner as in cycle 29 except for the substitution of BOC-O-Bz-L-serine as the amino acid derivative. This may be written:

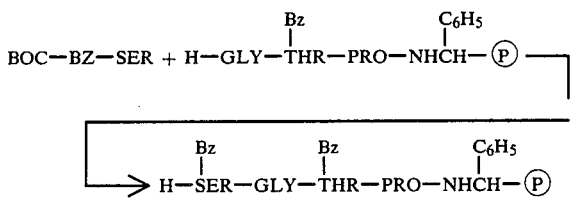

CYCLE 26

In cycle 26, the coupling and deprotection reactions are preformed as described in cycle 29 except that BOC-glycine is substituted as the amino acid reactant. These reactions through coupling and deprotection may be written as follows:

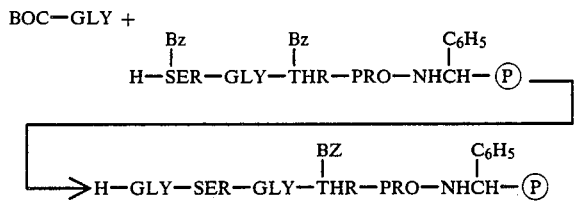

CYCLE 25

In this cycle, the coupling and deprotection reactions may be as in cycle 29 using the same amino acid reactant, resulting in the following compound:

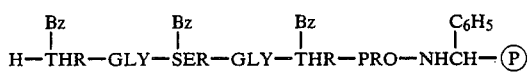

CYCLE 24

In cycle 24, the coupling reaction is performed using an active ester derivative of BOC-L-asparagine. The active ester procedure is used in place of the DCC coupling agent with BOC-L-asparagine or BOC-L-glutamine. The reaction using the active ester derivative of BOC-L-asparagine may be performed in the amount of 2 to 10 equivalents per free amine equivalent of BHA resin in dimethylformamide, mixtures of dimethylformamide with benzene, methylene chloride or chloroform or with equivalents thereof in the amount of 2 to 20 ml. of solvent per gram of BHA resin used initially.

Reaction times range from 1 to 72 hours. The reaction mixture may be removed from the BOC peptide resin by filtration after completion of the reaction as indicated by a ninhydrin test. The active ester derivatives employed may be 2-nitrophenyl esters, 4-nitrophenyl esters, pentafluorophenyl esters, or equivalents thereof. We use AE to designate the active ester portion of the derivative. The coupling reaction may be written:

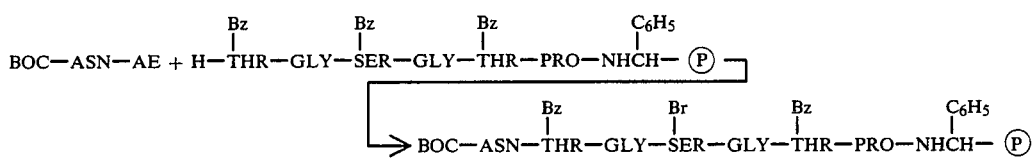

The deprotection reaction to remove the BOC group is performed as in cycle 30.

CYCLES 23-19

In each of cycles 23 to 19, the coupling and deprotection reactions may be conducted using the methods and proportions of reactants as in cycle 29, using BOC-O-BZ-L-threonine in cycle 23, BOC-Ω-T-L-arginine in cycle 22, BOC-L-proline in cycle 21, BOC-O-benzyl-L-threonine in cycle 20, and BOC-L-glutamine AE in cycle 19. The compound resulting from the completion of cycle 19 may be written:

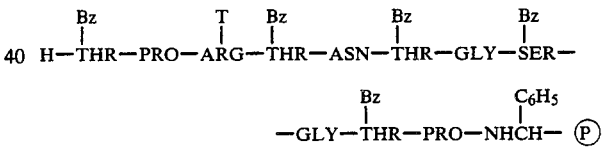

CYCLE 19

In cycle 19, the coupling and deprotection reactions may be performed using the methods and proportions of reactants as in cycle 24 using a BOC-L-glutamine active ester derivative as the amino acid derivative, resulting in the compound:

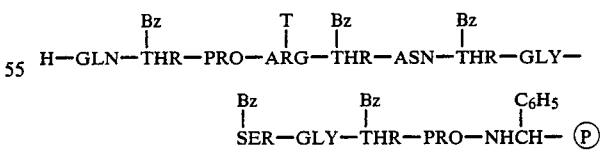

CYCLE 18

In cycle 18, the reactions are performed as in cycle 29 using BOC-L-leucine as the amino acid derivative. The compound resulting from cycle 18 is:

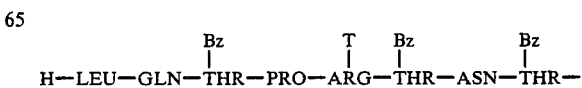

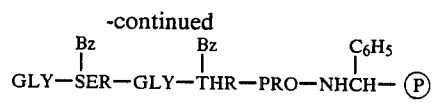

CYCLE 17

In cycle 17, we may use as the amino acid derivative BOC-ε-V-L-lysine. Otherwise, cycle 17 methods may be performed as in cycle 29 resulting in the compound:

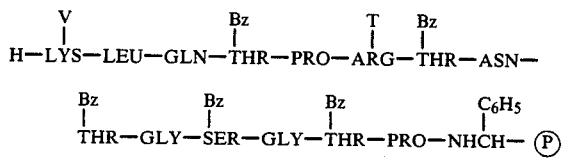

CYCLES 16–14

Cycles 16 to 14 may be performed as in cycle 29 except for the use of BOC-N(im)-V-L-histidine in cycle 16, BOC-L-leucine as the reactant in cycle 15 and BOC-L-glutamic acid BZ ester (BZ represents the same groups as it represents for serine and threonine) as the reactant in cycle 14, resulting in the following compound from cycle 14:

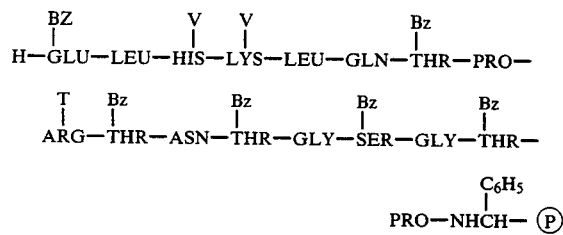

CYCLES 13–7

Cycle 13 may be performed identically to cycle 18 using BOC-L-glutamine-AE as the amino acid derivative. Cycles 12 to 6 may be performed as in cycle 29 except for the use of BOC-O-BZ-L-serine in cycle 12, BOC-L-leucine in cycle 11, BOC-ε-V-L-lysine in cycle 10, BOC-glycine in cycle 9, BOC-L-leucine in cycle 8, and BOC-L-glycine in cycle 7 resulting in the compound:

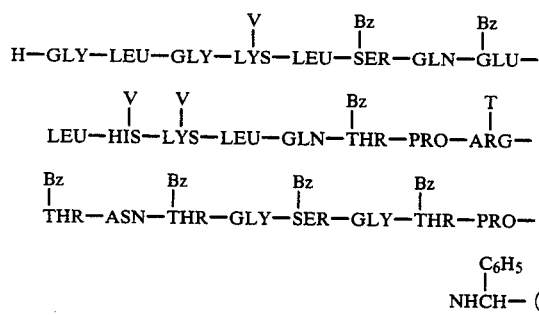

CYCLE 6

Cycle 6 may be performed as in cycle 29 except for the use of BOC-S-4-ethylthio-L-cysteine or equivalent for the amino acid derivative. The compound resulting from cycle 6 is described by the formula:

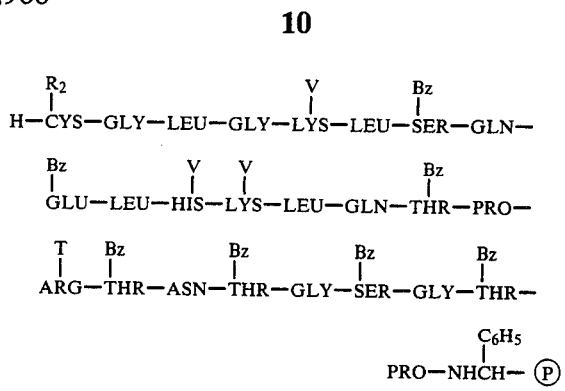

wherein $R_2$ is an alkylthio or a BZ group.

CYCLES 5–2

Cycles 5 to 2 may be performed as in cycle 29 except that BOC-O-BZ-L-threonine be used as the amino acid derivative in cycle 5, BOC-O-BZ-L-serine may be used as the amino acid derivative in cycle 4, and BOC-L-leucine may be used in cycle 3 as the amino acid derivative. Cycle 2 may be performed identically to cycle 24 using BOC-L-asparagine active ester. The compound resulting from cycle 2 is:

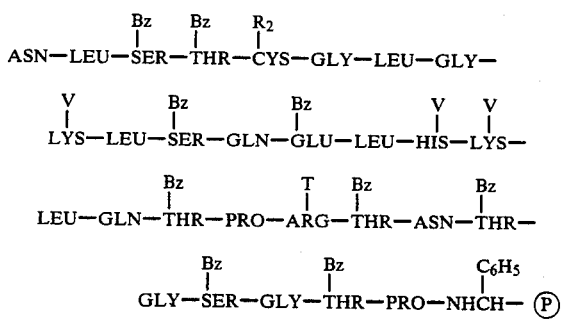

CYCLE 1

This cycle may be performed identically to cycle 6 using BOC-S-$R_1$-L-cysteine derivatives. The $R_1$ group chosen for the cysteine may be the same as used in cycle 6 or different. For example, if the derivative chosen for cycle 6 is BOC-S-ethylthio-L-cysteine, the derivative in cycle 1 may be BOC-S-4-methoxybenzyl-L-cysteine or if BOC-S-4-methoxybenzyl-L-cysteine was chosen for cycle 6, then this derivative or BOC-S-ethylthio-L-cysteine may also be used in cycle 1. The compounds resulting from cycle 1 are illustrated by the formula:

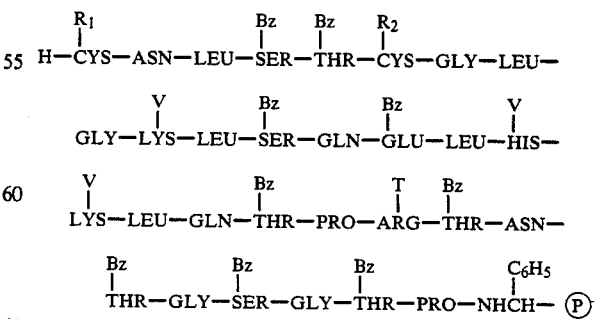

where $R_1$ is S-n-alkyl, CYS or Bz and $R_2$ is S-n-alkyl or Bz, $R_1$ being alkyl or CYS when $R_2$ is Bz and $R_1$ being Bz when $R_2$ is S-n-alkyl.

Cycle 1 represents the completion of the resin peptide, the resin peptide may be removed from the reaction vessel and dried in a vacuum. The weight of the resin peptide may be expected to be from 2.0 to 3.5 times weight of BHA resin used initially in the synthesis.

Resin Peptide Cleavage

The peptide is cleaved from the resin peptide resulting from cycle 1 by treatment with liquid hydrogen fluoride (HF). The HF cleavage reaction may be performed by treating a mixture of the resin peptide and anisole (0.5 to 5 ml. for each gram of resin peptide) with liquid HF (2 to 20 ml. for each gram of resin peptide) for 0.5 to 20 hours at −20 degrees to +15 degrees centigrade. After the reaction period, the excess HF may be removed by evaporation and the resulting mixture of peptide and resin beads may be extracted with organic solvent such as ethyl acetate, diethyl ether, benzene or the like to remove the anisole and residual HF. The peptide may be separated from the resin beads by extraction into aqueous acetic acid. The peptide at this stage is not cyclic but is the non-cyclic product without the cyclic disulfide bond between the cysteines at positions 1 and 6 in the molecule.

The HF treatment removes all blocking groups from the peptide, except the S-alkylthio blocking groups on the thiol function of cysteine residue at either position 1 or 6. The S-n-alkylthio-L-cysteine residue is stable to the HF cleavage procedure and remains intact throughout the cleavage and extraction procedures. The S-Bz-L-cysteine residue is cleaved by HF to yield a cysteine residue with a free thiol function. Both types of blocking groups have been employed during our synthesis in combination with each other at positions 1 and 6.

Thus, the peptides obtained after HF cleavage can be one of four types depending upon the blocking groups chosen for the thiol function of the cysteine derivative used during the resin peptide synthesis.

If BOC-S-Bz-L-cysteine derivatives are used in the resin peptide synthesis cycle 1 and BOC-S-n-alkylthio-L-cysteine is used in cycle 6, the peptide resulting after HF cleavage would be of Type I and would have a free thiol function at position 1 and have a S-n-alkylthio function on the cysteine residue at position 6. We call this a Type I peptide which is represented by the formula give as follows:

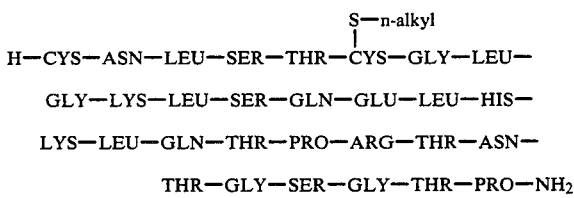

Conversely, if BOC-S-n-alkylthio-L-cysteine derivative is used in cycle 1 and the BOC-S-BZ-L-cysteines were used in position 6, the peptide resulting from the cleavage would be of Type II and would be represented by the formula:

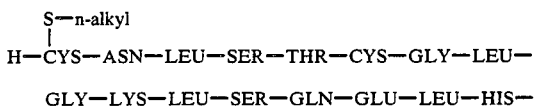

LYS—LEU—GLN—THR—PRO—ARG—THR—ASN—

THR—GLY—SER—GLY—THR—PRO—NH$_2$

In place of the protecting group S-n-alkyl at position 1 we may use a cysteine group (which with the cysteine at this position forms a cystine group) and when we do this we use a BZ group for protecting the cysteine at position 6. If Bis-BOC-L-cystine is used as the reactant in cycle 1 and the BOC-S-Bz-L-cysteine is used as the reactant in cycle 6, the peptide resulting from the cleavage will be of Type III and may be represented by the following formula:

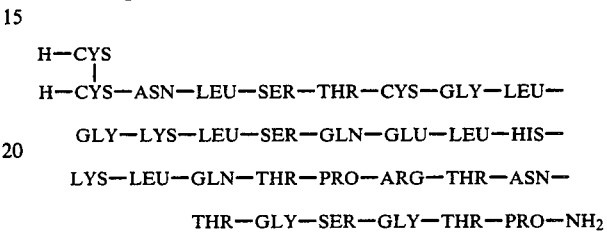

LYS—LEU—GLN—THR—PRO—ARG—THR—ASN—

THR—GLY—SER—GLY—THR—PRO—NH$_2$

If BOC-S-BZ-L-cysteine is used as the reactant in both positions 1 and 6, the peptide resulting from the cleavage will be of Type IV and represented by the following formula:

H-CYS-ASN-LEU-SER-THR-CYS-GLY-LEU-
GLY-LYS-LEU-SER-GLN-GLU-LEU-HIS-
LYS-LEU-GLN-THR-PRO-ARG-THR-ASN-
THR-GLY-SER-GLY-THR-PRO-NH$_2$

The conversion of Types I, II and III peptides to the cyclic disulfide peptides may be performed by diluting with distilled water the aqueous acetic acid solution of the crude peptides from HF cleavage to a final volume of 50 to 200 ml. per gram of resin peptide cleaved. The pH of this solution may be adjusted from 5 to 10 by the addition of ammonium hydroxide solution and the mixture may be stirred in a closed container under a stream of an inert gas such as nitrogen for about 2 to 48 hours. The reaction period can be stopped when the effluent gas stream no longer contains n-alkylmercaptan. The pH of the reaction mixture may be lowered to about 3.5 to 5.5 by the addition of glacial acetic acid.

The conversion to Type IV peptides to the cyclic disulfide peptide may be performed by the classical method known to the art in which the peptides are oxidized to join the ring structure to include in the ring the cysteines at positions 1 and 6.

Whether the intermediate peptides are of Type I, II, III or IV we may synthesize peptides having amino acid chains corresponding to any known calcitonin except for the deletion of amino acids at positions 2 and 22 and substitution of glycine in position 8. Such peptide synthesized as herein set forth, may be purified and found to have the same type of biological activity as the known calcitonin. Any calcitonin so synthesized is designated [Des-X$^2$-Gly$^8$-Des-Y$^{22}$]calcitonin, wherein X is serine or glycine and Y is phenylalanine or tyrosine. This is in accordance with the IUPAC-IUB method of nomenclature.

Purification Of The Crude [Des-Ser$^2$-Gly$^8$-Des-Tyr$^{22}$]Salmon Calcitonin The crude peptide solutions at pH 5.0 from the above synthesis may be concentrated using an ion-exchange procedure. The concentrate may be purified by a combination of gel-filtration procedures, ion-exchange chromatography methods and partition chromatography. The final purified product may be obtained from solution by freeze-drying as a fluffy white solid. The product gives the correct amino acid analysis for the desired peptide.

Following is the specific example of the preparation of the peptide.

EXAMPLE 1

Resin Activation

The BHA resin (5 g.) with an amine titer of 0.61 meg./g. was placed in the reacter vessel of a peptide synthesizer marketed by Vega Biochemicals of Tucson, Ariz. The resin was treated with 25 ml. of the following solvents filtering after each treatment:
Methylene chloride for 2 minutes
Chloroform for 2 minutes two times each
10% triethylamine in chloroform for 5 minutes two times each
Chloroform for 2 minutes
Methylene chloride for 2 minutes three times each

CYCLE 30

Coupling: The BHA resin, 25 ml. of methylene chloride and 1.31 g. (0.0061 moles) of BOC-L-proline was stirred for 10 minutes. 6.1 ml. of methylene chloride solution of dicyclohexylcarbodiimide (1 milliequivalent of DCC per 1 ml. of solution) was added to the reactor and the mixture agitated for 6 hours. The reaction mixture was removed from the reactor by filtration and the BOC-prolyl BHA resin subjected to the following successive 2 minute, 25 ml. washes, removing the wash by filtration each time:
Methylene chloride two times
Methyl alcohol two times
Methylene chloride three times Acetylation: The resin was then agitated with a mixture of 1.5 ml. of triethylamine (TEA), 1 ml. of acetic anhydride and 25 ml. of chloroform for 2 hours. The reaction mixture was removed by filtration and the resin subjected to the following 2 minute, 25 ml. washes:
Chloroform two times
Methyl alcohol two times
Methylene chloride three times Deprotection: The BOC-protected resin was agitated for 5 minutes with a mixture of 15 ml. of trifluoroacetic acid (TFA) and 15 ml. of methylene chloride. This mixture was removed by filtration and the resin was agitated with a second mixture of 15 ml. of TFA and 15 ml. of methylene chloride for 30 minutes. The reaction mixture was removed by filtration and the resin subject to the following 25 ml. washes:
Methylene chloride two times two minutes each
Methyl alcohol two times two minutes each
Chloroform two times two minutes each
10% TEA in chloroform two times ten minutes each
Chloroform two times two minutes each
Methylene chloride two times two minutes each The L-proline BHA resin was titrated to establish the amine or proline titer. This value was 0.55 milliequivalents of amine or proline per gram of resin.

CYCLE 29

Coupling: The L-prolyl resin, 25 ml. of methylene chloride and 1.64 g. (0.0053 mole) of BOC-O-benzyl-L-threonine were agitated for 10 minutes. Then 5.5 ml. of methylene chloride solution of dicyclohexylcarbodiimide (1 milliequivalent of DCC per 1 ml. of solution or a total of 0.0055 mole of DCC) was added to the reactor and the mixture agitated for 2 hours. The reaction mixture was removed from the reactor and the resin was subjected to the following successive 2 minute, 25 ml. washes, removing the wash by filtration each time.
Methylene chloride two times
Methyl alcohol two times
Methylene chloride three times
An isatin test was negative.

Deprotection: The deprotection procedure described in cycle 30 was repeated for this cycle.

CYCLES 28 THROUGH 25

The coupling and deprotection procedures used in these cycles were the same as in cycle 31 except that the following amino acid derivatives were used in place of the threonine derivative:
Cycle 28—0.93 g. (0.0053 mole) of BOC glycine
Cycle 27—1.55 g. (0.0053 mole) of BOC-O-benzyl-L-serine
Cycle 26—The reactant used was the same as cycle 28
Cycle 25—The reactant used was the same as cycle 29

CYCLE 24

Coupling: The peptide resin obtained from cycle 25 was washed twice with 25 ml. portions of dimethylformamide (DMF). The resin was then agitated for 24 hours with a solution of 2.82 g. (0.008 mole) of BOC-L-asparagine p-nitrophenyl ester in 35 ml. of DMF. The reaction mixture was filtered and the resin peptide subjected to two minute washes with two successive 25 ml. portions of the following solvents: DMF, methylene chloride, methanol, methylene chloride. Each individual solvent was removed by filtration. A ninhydrin test was negative.

Deprotection: The deprotection procedure used in cycle 30 was repeated.

CYCLE 23

Coupling and deprotection procedures were the same as in cycle 29 using the same reactants and amounts.

CYCLE 22

Coupling: The resin peptide obtained from cycle 25 was washed with two successive 25 ml. portions of DMF. The resin peptide was then agitated for 10 minutes with a mixture of 3.42 g. (0.008 mole) of BOC-N-$\Omega$-tosyl-L-arginine and 25 ml. of DMF. Then 8 ml. of DCC in methylene chloride (equivalent to 0.008 mole of DCC) was added and the mixture agitated for 6 hours. The reaction mixture was removed by filtration. The resin peptide was subjected to two minute washes with two successive 25 ml. portions of the following solvents: DMF, methylene chloride, methyl alcohol, methylene chloride. The ninhydrin test was negative.

Deprotection: The deprotection used in cycle 30 was repeated.

CYCLE 21

Coupling: The peptide resin obtained from cycle 22 was agitated for 10 minutes with 1.72 g. (0.008 mole) of BOC-L-proline and 25 ml. of methylene chloride. 8 ml. of DCC in methylene chloride (equivalent to 0.008 mole of DCC) was added and the mixture agitated for 6 hours. The reaction mixture was removed by filtration and the resin peptide subjected to two minute washes with two successive 25 ml. portions of the following solvents: methylene chloride, methyl alcohol, methylene chloride. Each individual wash was removed by filtration. The ninhydrin test was negative.

Deprotection: The deprotection used in cycle 30 was repeated.

CYCLE 20

The coupling and deprotection procedures used in this cycle was the same as in cycle 29 except that in the coupling reaction the following amino acid derivative was used in place of BOC-L-proline.
Cycle 20—1.64 g. (0.0053 mole) BOC-O-benzyl-L-threonine

CYCLE 19

This procedure is the same as cycle 24 except that 2.94 g. (0.008 mole) of BOC-L-glutamine p-nitrophenyl ester is used in place of the asparagine derivative.

CYCLES 18 THROUGH 14

The procedure is the same as used in cycle 29 except that the following amino acid derivatives were used in place of the threonine derivative:
Cycle 18—1.32 g. (0.0053 mole) of BOC-L-leucine
Cycle 17—2.20 g. (0.0053 mole) of BOC-ε-2-chloro bonzyloxy-L-lysine
Cycle 16—2.06 g. (0.0053 mole) of BOC-N(im)-carbobenzyloxy-L-histidine
Cycle 15—See cycle 19
Cycle 14—1.79 g. (0.0053 mole) of BOC-L-glutamic acid-γ-benzyl ester

CYCLE 13

Same as cycle 19.

CYCLE 12

The procedure used was the same as was used in cycle 20 except that in the coupling reaction 2.36 g. (0.008 mole) of BOC-O-benzyl-L-serine was used in place of the proline derivative.

CYCLES 11 THROUGH 8

The procedures used were the same as used in cycle 29 except in the coupling reactions the following amine acid derivatives were used in place of the threonine derivative.
Cycle 11—Same reactants as used in cycle 18
Cycle 10—The reactants were the same as in cycle 17
Cycle 9—Same reactants as used in cycle 28
Cycle 8—Same reactants as used in cycle 11

CYCLE 7

Coupling: The resin peptide from cycle 8 was agitated for 10 minutes with 1.74 g. (0.008 mole) of BOC-L-glycine and 25 ml. of methylene chloride. Then 8 ml. of DCC in methylene chloride (equivalent to 0.008 mole of DCC) was added and the mixture agitated for 16 hours. The reaction mixture was removed by filtration. The resin peptide was subjected to two minute washes with two successive 25 ml. portions of the following solvents: methylene chloride, methyl alcohol, methylene chloride. Each individual wash was removed by filtration.

Deprotection: See cycle 29.

CYCLE 6

The procedure was the same as used in cycle 29 except that in the coupling reaction 1.59 g. (0.0053) of BOC-S-ethylthio-L-cysteine was used in place of the threonine derivative.

CYCLE 5

The reactants and procedures used were the same as cycle 29.

CYCLE 4

The reactants and procedures used were the same as cycle 27.

CYCLE 3

The reactants and procedures used were the same as cycle 18.

CYCLE 2

The reactants and procedures used were the same as cycle 24.

CYCLE 1

The reactants and procedures used were the same as cycle 29 except that 1.81 g. (0.0053 mole) of BOC-S-p-methoxybenzyl-L-cysteine was used in place of the threonine derivative.

After completion of cycle 1, the resin peptide was washed with two successive 25 ml. portions of n-hexane. The peptide material was removed from the reactor and dried in an electric vacuum oven at 40 degrees centigrade and 0.1 mm. of Hg for 24 hours.

Cleavage with Hydrogen Fluoride

The dried resin peptide (2 g.) and 2 ml. of anisole were placed in a Teflon reaction vessel. The vessel equipped with a Teflon-coated magnet stirrer was placed in a dry ice-acetone bath and 15 ml. of hydrogen fluoride gas was condensed into the vessel. This mixture was stirred at 0 degrees centigrade in an ice bath for 1 hour. The hydrogen fluoride was removed by evaporation at reduced pressure. The residue was triturated with six 25 ml. portions of ethyl acetate. The peptide was extracted from the resin beads with 120 ml. of 0.1 molar aqueous acetic solution.

Cyclization Of The Peptide

The aqueous acetic acid extract obtained from hydrogen fluoride cleavage was diluted to 200 ml. by addition of 80 ml. of distilled water. The pH of the solution was adjusted to 7.5 by the addition of concentrated ammonium hydroxide. The solution was stirred in a closed vessel under a stream of nitrogen for 24 hours. At this time no ethyl mercaptan could be detected in the emerging nitrogen stream. The ethyl mercaptan content of the nitrogen stream was measured by passing the stream through a solution of Ellman's reagent [Ellman, G. L., *Arch. Biochem. Biophys.*, 82, 70–7 (1969)]. The pH of the reaction mixture was adjusted to 5.0 by addition of glacial acetic acid.

Purification Of The Crude [Des-Ser$^2$-Gly$^8$-Des-Tyr$^{22}$]SCT

The 200 ml. of solution from the above synthesis at pH 5.0 was concentrated using a SP-25 ion-exchange column. The 25 ml. concentrate removed from the column with 0.7 molar sodium chloride solution was desalted and purified by passing through a Sephadex G-25 (fine) gel-filtration column and eluting with 0.03 molar aqueous acetic acid solution. The [Des-Ser²-Gly⁸-Des-Tyr²²]SCT fraction from this column was adjusted to pH 6 by the addition of ammonium hydroxide solution. This solution was further purified by ion-exchange chromatography using a Whatman CM-52 column eluted with ammonium acetate buffer. The product was further purified by partition chromatography using a Sephadex G-25 fine column and the solvent system: n-butanol, ethanol, 0.2N ammonium acetate containing 0.04% acetic acid (4-1-5). The product elutes from the column at an Rf value of 0.30. The fractions containing the product were combined and the n-butanol removed by evaporation. The product was recovered by lyophilization. The solid was then gel-filtered on a Sephadex G-25 (fine) column with 0.2M acetic acid solution. The purified peptide fraction was collected and lyophilized. The product was obtained as a fluffy white solid. Amino acid analysis of the product gave the following ratios with the theoretical values given in parenthesis: Asp 2.0 (2), Thr 5.2 (5), Ser 2.9 (3), Glu 2.9 (3), Pro 2.0 (2), Gly 4.0 (4), Leu 5.0 (5), His 0.97 (1), Lys 2.0 (2), Arg 0.98 (1), NH₃ 5.1 (5).

Biological Assay Of Calcitonin Analogs In Vivo

The biological potency of [Des-Serine²-Glycine⁸-Des-Tyrosine²²]salmon calcitonin was determined by comparing the reduction of serum calcium concentration which followed administration by graded doses of [Des-Ser²-Gly⁸-Des-Tyr²²]SCT and synthetic salmon calcitonin standard. Rats were divided into four groups of seven animals, and each group was assigned at random to a dose of standard or test solution. Low and high doses were chosen from the linear portion of the dose-response curve. For the salmon calcitonin standard, the values were 0.7 and 2.1 ng. peptide/100 g. body weight (BW). This dose approximates 3 and 9 MU/100 g. BW. Peptides were given by subcutaneous injection (0.2 ml/100 g. BW) and blood was withdrawn 1 hour later for serum calcium determination. Sera are processed and analyzed within two hours of collection. Results were analyzed within two hours of collection. Results were analyzed by a 2×2 parallel line assay [Gaddum, J. H., *J. Pharm. Pharmacol.*, 6, 345 (1953)]. The standard salmon calcitonin used was independently determined to contain greater than 4,000 IU/mg. [Des-Ser²-Gly⁸-Des-Tyr²²]SCT assayed at 6900 IU/mg.

While only certain embodiments of our invention have been described in specific detail it will be apparent to those skilled in this art that many other specific embodiments may be practiced and many changes may be made, all within the spirit of the invention and the scope of the appended claims.

What is claimed:

1. A peptide having the structure:

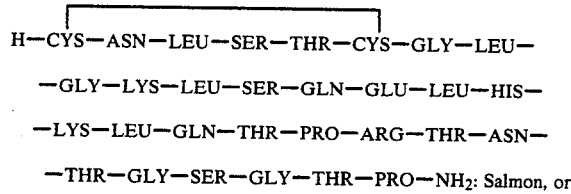

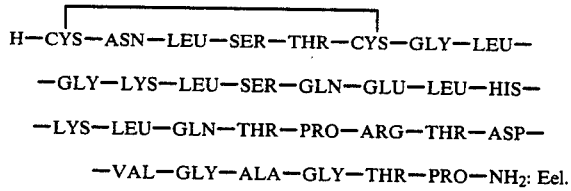

2. A peptide having the structure:

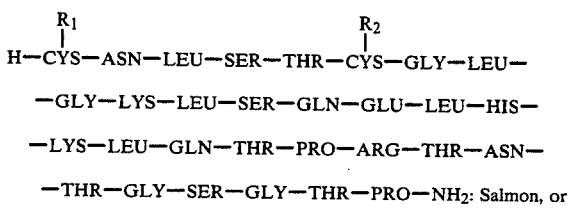

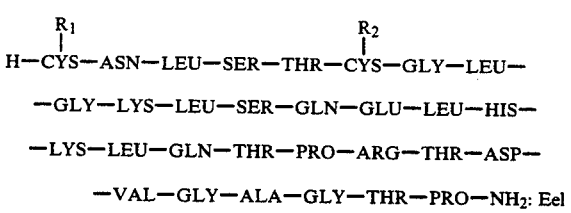

where $R_1$ is S-n-alkyl, Cys or H and $R_2$ is S-n-alkyl or H, $R_1$ being S-n-alkyl, Cys or H when $R_2$ is H and $R_2$ being S-n-alkyl or H when $R_1$ is H, wherein the alkyl group is methyl, ethyl, propyl, or butyl.

3. Des-Ser²-Gly⁸-Des-Tyr²²-Calcitonin wherein the calcitonin is a salmon calcitonin analog.

4. Des-Ser²-Gly⁸-Des-Tyr²²-Calcitonin wherein the calcitonin is an eel calcitonin analog.

* * * * *